United States Patent
Orosco et al.

(10) Patent No.: US 8,748,676 B2
(45) Date of Patent: *Jun. 10, 2014

(54) PROCESS FOR PURIFYING A CRUDE ETHANOL PRODUCT

(75) Inventors: Adam Orosco, Houston, TX (US); Lincoln Sarager, Houston, TX (US); R. Jay Warner, Houston, TX (US); Radmila Jevtic, Pasadena, TX (US)

(73) Assignee: Celanese International Corporation, Dallas, TX (US)

( * ) Notice: Subject to any disclaimer, the term of this patent is extended or adjusted under 35 U.S.C. 154(b) by 215 days.

This patent is subject to a terminal disclaimer.

(21) Appl. No.: 13/197,748

(22) Filed: Aug. 3, 2011

(65) Prior Publication Data

US 2013/0035516 A1    Feb. 7, 2013

(51) Int. Cl.
  *C07C 27/04*   (2006.01)
(52) U.S. Cl.
  USPC ............................ 568/885; 568/880; 568/881
(58) Field of Classification Search
  None
  See application file for complete search history.

(56) References Cited

U.S. PATENT DOCUMENTS

| | | | |
|---|---|---|---|
| 2,882,244 A | 4/1959 | Milton | |
| 3,102,150 A | 8/1963 | Hunter et al. | |
| 3,130,007 A | 4/1964 | Breck | |
| 3,408,267 A | 10/1968 | Miller, at al. | |
| 3,445,345 A | 5/1969 | Katzen et al. | |
| 3,478,112 A | 11/1969 | Karl et al. | |
| 3,990,952 A | 11/1976 | Katzen et al. | |
| 4,275,228 A | 6/1981 | Gruffaz et al. | |
| 4,306,942 A | 12/1981 | Brush et al. | |
| 4,319,058 A | 3/1982 | Kulprathipanja et al. | |
| 4,379,028 A | 4/1983 | Berg et al. | |
| 4,398,039 A | 8/1983 | Pesa et al. | |
| 4,454,358 A | 6/1984 | Kummer et al. | |
| 4,465,854 A | 8/1984 | Pond et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,517,391 A | 5/1985 | Ludwig et al. | |
| 4,551,560 A * | 11/1985 | Rizkalla | 568/465 |
| 4,569,726 A | 2/1986 | Berg et al. | |
| 4,626,321 A | 12/1986 | Grethlein et al. | |
| 4,678,543 A | 7/1987 | Houben et al. | |
| 4,692,218 A | 9/1987 | Houben et al. | |
| 4,777,303 A | 10/1988 | Kitson et al. | |
| 4,842,693 A | 6/1989 | Wheldon | |
| 4,886,905 A | 12/1989 | Larkins et al. | |
| 4,961,826 A | 10/1990 | Grethlein et al. | |
| 4,985,572 A | 1/1991 | Kitson et al. | |
| 4,990,655 A | 2/1991 | Kitson et al. | |
| 4,994,608 A | 2/1991 | Torrence et al. | |
| 5,001,259 A | 3/1991 | Smith et al. | |
| 5,026,908 A | 6/1991 | Smith et al. | |
| 5,035,776 A | 7/1991 | Knapp | |
| 5,124,004 A | 6/1992 | Grethlein et al. | |
| 5,144,068 A | 9/1992 | Smith et al. | |
| 5,149,680 A | 9/1992 | Kitson et al. | |
| 5,185,481 A | 2/1993 | Muto et al. | |
| 5,250,271 A | 10/1993 | Horizoe et al. | |
| 5,362,918 A | 11/1994 | Aizawa et al. | |
| 5,449,440 A | 9/1995 | Rescalli et al. | |
| 5,502,248 A | 3/1996 | Funk et al. | |
| 5,527,969 A | 6/1996 | Kaufhold et al. | |
| RE35,377 E | 11/1996 | Steinberg et al. | |
| 5,599,976 A | 2/1997 | Scates et al. | |
| 5,770,770 A | 6/1998 | Kim et al. | |
| 5,821,111 A | 10/1998 | Gaddy et al. | |
| 5,861,530 A | 1/1999 | Atkins et al. | |
| 5,973,193 A | 10/1999 | Crane et al. | |
| 5,993,610 A | 11/1999 | Berg | |
| 6,040,474 A | 3/2000 | Jobson et al. | |
| 6,093,845 A | 7/2000 | Van Acker et al. | |
| 6,143,930 A | 11/2000 | Singh et al. | |
| 6,232,352 B1 | 5/2001 | Vidalin et al. | |
| 6,375,807 B1 * | 4/2002 | Nieuwoudt et al. | 203/19 |
| 6,472,555 B2 | 10/2002 | Choudary et al. | |
| 6,509,180 B1 | 1/2003 | Verser et al. | |
| 6,627,770 B1 | 9/2003 | Cheung et al. | |

(Continued)

FOREIGN PATENT DOCUMENTS

| | | |
|---|---|---|
| EP | 0104197 | 4/1984 |
| EP | 0167300 | 1/1986 |

(Continued)

OTHER PUBLICATIONS

Kita H., et al., "Synthesis of a Zeolite NAA Membrane for Pervaporation of Water/Organic Liquid Mixtures", Journal of Materials Science Letters, vol. 14, Jan. 1, 1995, pp. 206-208.

(Continued)

*Primary Examiner* — Sudhakar Katakam

(57) ABSTRACT

In one embodiment, the invention is to a process for purifying a crude ethanol product. The process comprises the step of hydrogenating acetic acid in a first reaction zone in the presence of a first catalyst to form the crude ethanol product comprising ethanol, acetaldehyde, acetic acid, water, and acetal. The process further comprises the step of separating at least a portion of the crude ethanol product into a refined ethanol stream and a by-product stream. The refined ethanol stream comprises ethanol and acetaldehyde; and the by-product stream comprises acetic acid and a substantial portion of the water from the crude ethanol product. The process further comprises the step of hydrolyzing in a second reaction zone at least a portion of the acetal.

27 Claims, 3 Drawing Sheets

(56) References Cited

U.S. PATENT DOCUMENTS

| | | |
|---|---|---|
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,765,110 B2 | 7/2004 | Warner et al. |
| 6,768,021 B2 | 7/2004 | Horan et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,115,772 B2 | 10/2006 | Picard et al. |
| 7,208,624 B2 | 4/2007 | Scates et al. |
| 7,297,236 B1 | 11/2007 | Vander Griend et al. |
| 7,351,559 B2 | 4/2008 | Verser et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,863,489 B2 | 1/2011 | Johnston et al. |
| 7,884,253 B2 | 2/2011 | Stites et al. |
| 7,888,082 B2 | 2/2011 | Verser et al. |
| 2003/0013908 A1 | 1/2003 | Horan et al. |
| 2006/0019360 A1 | 1/2006 | Verser et al. |
| 2006/0127999 A1 | 6/2006 | Verser et al. |
| 2007/0106246 A1 | 5/2007 | Modesitt |
| 2007/0270511 A1 | 11/2007 | Melnichuk et al. |
| 2008/0135396 A1 | 6/2008 | Blum |
| 2008/0193989 A1 | 8/2008 | Verser et al. |
| 2009/0005588 A1 | 1/2009 | Hassan et al. |
| 2009/0023192 A1 | 1/2009 | Verser et al. |
| 2009/0069609 A1 | 3/2009 | Kharas et al. |
| 2009/0281354 A1 | 11/2009 | Mariansky et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0197485 A1 | 8/2010 | Johnston et al. |
| 2011/0082322 A1* | 4/2011 | Jevtic et al. .......... 568/885 |
| 2011/0275862 A1 | 11/2011 | Johnston et al. |

FOREIGN PATENT DOCUMENTS

| | | |
|---|---|---|
| EP | 0400904 | 5/1990 |
| EP | 0372847 | 6/1990 |
| EP | 0456647 | 11/1991 |
| EP | 2060553 | 5/2009 |
| EP | 2060555 | 5/2009 |
| EP | 2072487 | 6/2009 |
| WO | WO 83/03409 | 10/1983 |
| WO | WO 2007/003897 | 1/2007 |
| WO | WO 2009/063176 | 5/2009 |
| WO | WO 2009/105860 | 9/2009 |
| WO | WO 2010/055285 | 5/2010 |
| WO | WO 2011/097193 | 8/2011 |
| WO | WO 2011/097219 | 8/2011 |
| WO | WO 2012/006499 | 1/2012 |

OTHER PUBLICATIONS

Marian Simo, et al., "Adsorption/Desorption of Water and Ethanol on 3A Zeolite in Neo-Adiabatic Fixed Bed", Industrial and Engineering Chemistry Research, vol. 48, No. 20, Sep. 25, 2009, pp. 9247-9260.

International Search Report and Written Opinion for PCT/US2011/046501 mailed Jul. 30, 2012.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

* cited by examiner

US 8,748,676 B2

PROCESS FOR PURIFYING A CRUDE ETHANOL PRODUCT

FIELD OF THE INVENTION

The present invention relates generally to processes for producing alcohols and, in particular, to reduced energy processes for recovering ethanol.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. In addition to petrochemical feed stocks synthesis methods, starchy materials, as well as cellulose materials, may be converted to ethanol by fermentation. Fermentation methods are typically employed for production of consumable ethanol, although the ethanol thus produced may also be suitable for fuels. Fermentation of starchy or cellulose materials also competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. As examples, esters and/or acetals, e.g., diethyl acetal, may be formed via these side reactions. These impurities 1) limit the production of ethanol; and 2) impede the purification of the ethanol in the crude reaction product. Typically, the separation of esters and acetals from ethanol has proven to necessitate excessive resource requirements, e.g., high energy and/or large numbers of trays.

In view of these shortcomings, a need remains for improved separation schemes, which provide the ability to more effectively separate impurities from ethanol.

SUMMARY OF THE INVENTION

In one embodiment, the invention is to a process for purifying a crude ethanol product comprising ethanol, acetaldehyde, acetic acid, water, and acetal, e.g., diethyl acetal. The process comprises the step of hydrogenating acetic acid in a first reaction zone in the presence of a first catalyst to form the crude ethanol product. The process further comprises the step of separating at least a portion of the crude ethanol product into a refined ethanol stream and a by-product stream. The refined ethanol stream comprises ethanol and acetaldehyde and the by-product stream comprises acetic acid and a substantial portion of the water from the crude ethanol product. The process further comprises the step of hydrolyzing at least a portion of the acetal. Preferably, this step is conducted in a second reaction zone, which may comprise a second catalyst.

In another embodiment, the separating step is conducted in a first column. The first column yields a first distillate comprising ethanol and acetaldehyde and a first residue comprising acetic acid. In a preferred embodiment, the first distillate is separated in a second column to yield a second distillate comprising acetaldehyde and a second residue comprising ethanol. In some of these embodiments, the second column comprises the second reaction zone. In another embodiment, the separating step is conducted via a membrane separation unit.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
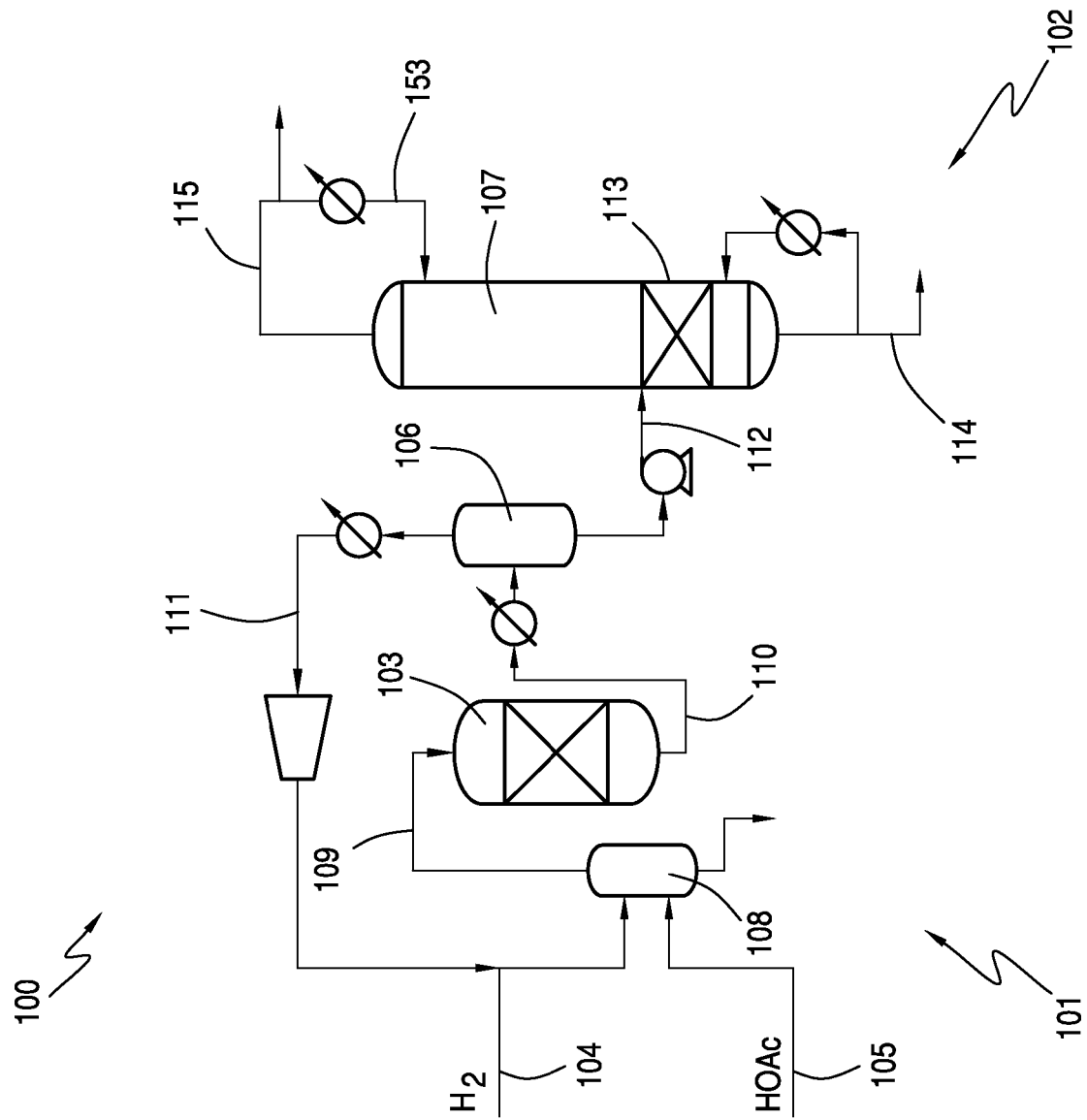
FIG. 1 is a schematic diagram of a hydrogenation/purification system in accordance with an embodiment of the present invention.

The present invention relates to processes for recovering ethanol produced by hydrogenating acetic acid, in particular to the removal of acetals from a crude ethanol product. The hydrogenation reaction may be conducted in a first reaction zone in the presence of a first catalyst. This reaction yields a crude ethanol product that comprises ethanol, acetaldehyde, water, unreacted acetic acid, ethyl acetate, and other impurities such as acetals, e.g., diethyl acetal, ethyl propyl acetal, ethyl butyl acetal and hemiacetals thereof. Generally speaking, it is desirable to remove such impurities from the crude ethanol product. In some embodiments, the crude ethanol product contains acetals in an amount greater than 0.0005 wt. % based on the total weight of the feed stream, e.g., greater than 0.01 wt. % or greater than 0.1 wt. %. In terms of ranges, the amount of acetals in the crude ethanol product may be from 0.0005 wt. % to 1 wt. % based on the total weight of the crude ethanol product, e.g., from 0.001 wt. % to 1 wt. % or from 0.01 wt. % to 1 wt. %. In terms of upper limits, the crude ethanol product comprises less than 1 wt % acetals, e.g., less than 0.1 wt. % acetals or less than 0.05 wt. %.

It has surprisingly and unexpectedly been found that at least a portion of the acetals in the crude ethanol product may be hydrolyzed, preferably to yield additional ethanol and or aldehyde. The hydrolysis of the acetals contributes to improved operating efficiencies. In addition to the hydrolyzing step, the processes of the present invention further comprise the step of separating the crude ethanol product into a refined ethanol stream comprising ethanol and acetaldehyde and a by-product stream comprising water and unreacted acetic acid and a substantial portion of the water in the crude ethanol product is separated into the by-product stream. Advantageously, this inventive combination of steps 1) improves overall ethanol production and 2) reduces energy requirements to recover ethanol from the crude ethanol product.

To separate the crude ethanol product, the processes of the present invention may employ a separation zone comprising one or more separation units. Any suitable separation units may be used and these suitable separation units are not limited to those mentioned herein. In a preferred embodiment, the separation unit(s) are distillation columns. The first separation unit yields the refined ethanol stream and the by-product stream. In a preferred embodiment, the first separation unit is a first distillation column, e.g., a reactive distillation column, and the resultant refined ethanol stream comprises the first distillate and the resultant by-product stream comprises the first residue. In this case, the first residue comprises a substantial portion of the water that was initially in the crude ethanol product. In one embodiment, the first separation unit is operated such that minor amounts, if any, acetic acid is carried over in the refined ethanol stream and minor amounts, if any, ethanol is leaked into the by-product stream.

The present invention beneficially removes a substantial portion of water from the crude ethanol product via the by-product stream, e.g., the first residue, as opposed to the refined ethanol stream, e.g., the first distillate, which significantly reduces the energy requirement for the separation process. The substantial portion of the water that is removed from the crude ethanol product and is present in the by-product stream may vary depending on the composition of the crude ethanol product, which is a result of the acetic acid conversion and selectivity to ethanol. In one embodiment, 30 to 90% of the water in the crude ethanol product is removed in the residue, e.g., from 40 to 88% of the water or from 50 to 84% of the water. Removing less water in the residue may increase acetic acid carry over in the distillate. In addition, leaving too much water in the residue may also cause increases in ethanol leakage into the residue. Also, depending on the conversion, the energy requirement may also increase when too much water is left in the distillate. Preferably, a majority of the water in the crude ethanol product that is fed to the first separation unit may be removed in the by-product stream, for example, up to about 90% of the water from the crude ethanol product, e.g., up to about 75%. In some embodiments, with lower conversions of acetic acid and/or selectivity, the substantial portion of water withdrawn in the by-product stream may be from 30% to 80%, e.g., from 40% to 75%.

As discussed above, in accordance with the present invention, the acetal in the crude ethanol product are hydrolyzed. Preferably, the hydrolysis is conducted in a second reaction zone. The second reaction zone, in one embodiment, is different from the first reaction zone, which is used to conduct the acetic acid hydrogenation reaction. The acetal hydrolyzes to form the respective alcohol and/or aldehyde. As an example, diethyl acetal may hydrolyze to form additional ethanol and/or acetaldehyde. In this case, the "additional" ethanol and/or acetaldehyde is ethanol and/or acetaldehyde that is formed in the hydrolysis reaction and after the hydrogenation reaction. The acetal in the crude ethanol product is preferably hydrolyzed such that any stream exiting the separation zone, including any streams that may be recycled to the first reaction zone from the separation zone, contains less acetal, on a weight basis, than is present in the crude ethanol product. As one example, the weight ratio of the amount of acetal in the crude ethanol product versus the amount of acetal exiting the separation zone preferably is from 100:1 to 2:1, e.g., from 50:1 to 5:1 or from 25:1 to 8:1. As a result of the hydrolysis and separation steps of the present invention, both overall ethanol yields and separation efficiencies are improved.

In some embodiments, the hydrolysis may be conducted over a catalyst, e.g., a second catalyst, which is separate from the first catalyst. For example, the second reaction zone may comprise the second catalyst. Acidic catalysts are preferred for the hydrolysis reaction. Without being bound by theory, it is believed that residual acid in the crude ethanol product may act as a catalyst for the hydrolysis reaction. Other suitable catalysts, however, may also be employed. The ion exchange resin reactor bed may comprise a strongly acidic heterogeneous or homogenous catalyst, such as for example a Lewis acid, strongly acidic ion exchange catalyst, inorganic acids, and methanesulfonic acid. Exemplary catalysts include Amberlyst™ 15 (Rohm and Haas Company, Philadelphia, U.S.A.), Amberlyst™ 70, Dowex-M-31 (Dow Chemical Company), Dowex Monosphere M-31 (Dow Chemical Company), and Purolite CT type Catalysts (Purolite International SRL). A catalyst, however, is not required to conduct the hydrolysis step. In one embodiment, the resonance time is sufficient to hydrolyze the acetal. In another embodiment, the hydrolysis reaction may proceed when sufficient acetic acid is present. The hydrolysis may be performed in any phase, with the liquid phase being preferred.

In some embodiments, the second reaction zone is disposed in one or more of the separation units, e.g., in one or more columns. For example, the hydrolysis may be performed in a reactive distillation column that concurrently performs the separation step and the hydrolysis step. In such a situation, the distillation column comprises the second reaction zone, e.g., the second reaction zone is within the distillation column. In these cases, the total of both streams exiting the column contains less acetal, on a weight basis, than is present in the feed directed to the separation zone, i.e., the crude ethanol product. The weight ratio of the amount of acetal in the crude ethanol product versus the amount of acetal in the distillate and residue of the column preferably is from 100:1 to 2:1, e.g., from 50:1 to 5:1 or from 25:1 to 8:1. In one embodiment, the overhead distillate of the first column may contain less than 5 wt. % acetal based on the total weight of the distillate, e.g., less than 2 wt. % or less than 1 wt. %. The residue of the first column may contain less than 0.5 wt. % acetal based on the total weight of residue, e.g., less than 0.001 wt. % or less than 0.0001 wt. %. Preferably substantially no detectable acetal is present in the residue of the first column. The combined weight amounts of acetal in the distillate and residue of the first column is preferably less than the amount of acetal in the feed directed to the first column. The reduction of the amount of acetal in the feed, as compared to the amount of acetal in the distillate, may be reduced by at least 50%, e.g., at least 75% or at least 90%. The reduction of the amount of acetal in the feed, as compared to the amount of acetal in the combined total of the distillate and residue may be reduced by at least 50%, e.g., at least 75% or at least 90%. Although, hydrolysis is discussed with respect to the first column, the same discussion applies to other separation units and/or columns that may be present in the separation zone. For example, in one embodiment, the separation zone comprises a first column and a second column and the second reaction zone is disposed in the second column.

In one embodiment, the second reaction zone comprises a reactor, e.g., a reactor bed. Preferably, the second reaction zone comprises an ion exchange resin reactor bed, which hydrolyzes acetal present in the crude ethanol product or in any subsequent intermediate distilled streams of the crude ethanol product. The ion exchange resin bed may comprise a catalyst as discussed above. Preferably, the ion exchange resin catalyst employed in the reactor bed comprises a solid acid catalyst or an acid ion exchange catalyst. In another embodiment, the ion exchange resin may be located within one or more distillation columns, e.g., in the first column and/or in the second column. In one embodiment, the refined ethanol stream, e.g., the overhead distillate of the first column, is directed to an ion exchange resin reactor bed to hydrolyze acetal that is present. Ethanol, acetaldehyde and/or acetic acid produced by the hydrolysis reaction(s) may be returned to the first reaction zone or may be further processed in one or more distillation columns.

Ion exchange resin reactor beds, in other embodiments, may be located externally to any of the distillation columns or within the distillation columns.

In an exemplary embodiment, the energy requirements by the first separation unit, e.g., the first column, in the process according to the present invention may be less than 5.5 MMBtu per ton of refined ethanol, e.g., less than 4.5 MMBtu per ton of refined ethanol or less than 3.5 MMBtu per ton of refined ethanol. In some embodiments, the process may operate with higher energy requirements provided that the total energy requirement is less than the energy required to remove most of the water from the crude ethanol product in the distillate as opposed to the residue, e.g. more than 65% of the water in the crude ethanol product. Additional energy is required to operate a first column that removes more water in either the distillate and/or residue. The energy requirements for the first column may increase rapidly when the water concentration in the distillate approaches the azeotropic amount, e.g., from about 4 wt. % to about 7 wt. %. To achieve these low water concentrations an increase of the reflux ratio is required and results in an increase of the energy demands on the column. For example, removing additional water, so that more than 90% of the water is removed in the residue, requires a high reflux ratio of greater than 5:1, greater than 10:1 or greater than 30:1. This may place additional energy demands on the distillation column.

The by-product stream may comprise at least 85% of the acetic acid from the crude ethanol product, e.g., at least 90% and more preferably at least about 100%. In terms of ranges, the by-product stream preferably comprises from 85% to 100% of the unreacted acetic acid from the crude ethanol product, and more preferably from 90% to 100%. In one embodiment, substantially all of the unreacted acetic acid is recovered in the by-product stream. By removing substantially all of the unreacted acetic acid from the crude ethanol product, the process, in some aspects, does not require further separation of acetic acid from the ethanol product. In this aspect, the ethanol product may contain some acetic acid, e.g., trace amounts of acetic acid.

The composition of the by-product stream may vary depending on acetic acid conversion, as discussed below, as well as the composition of the crude ethanol product and separation conditions in the separation unit(s). Depending on the composition, the by-product stream may be: (i) entirely or partially recycled to the hydrogenation reactor, (ii) separated into acid and water streams, (iii) treated with a solvent in a weak acid recovery process, (iv) reacted with an alcohol to consume the unreacted acetic acid, or (v) disposed to a waste water treatment facility.

Hydrogenation of Acetic Acid

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507, 562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 1 to 30 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Ethanol Recovery

Figure 2:
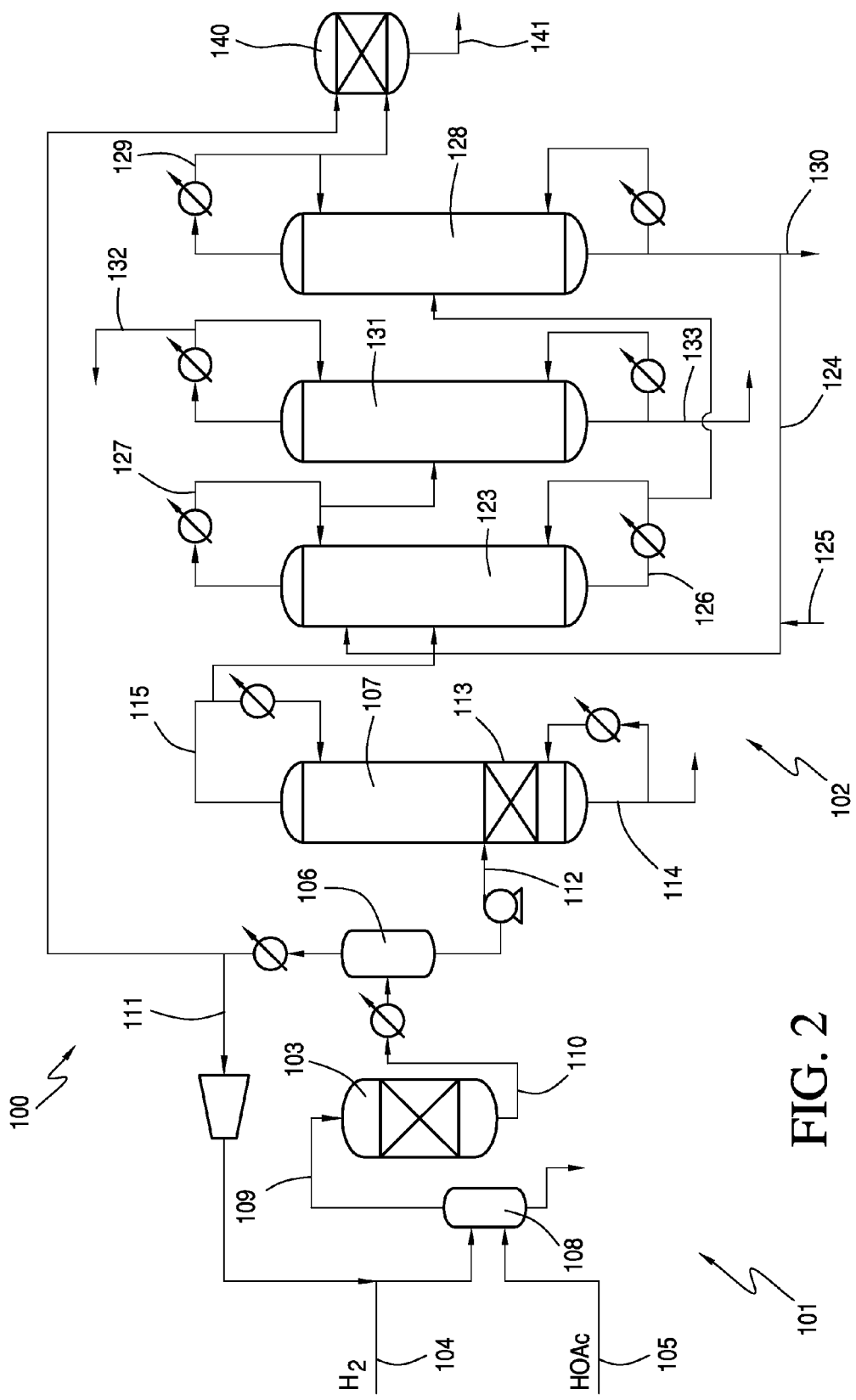
FIG. 2 is a schematic diagram of a hydrogenation/purification system having multiple columns in accordance with one embodiment of the present invention.
Figure 3:
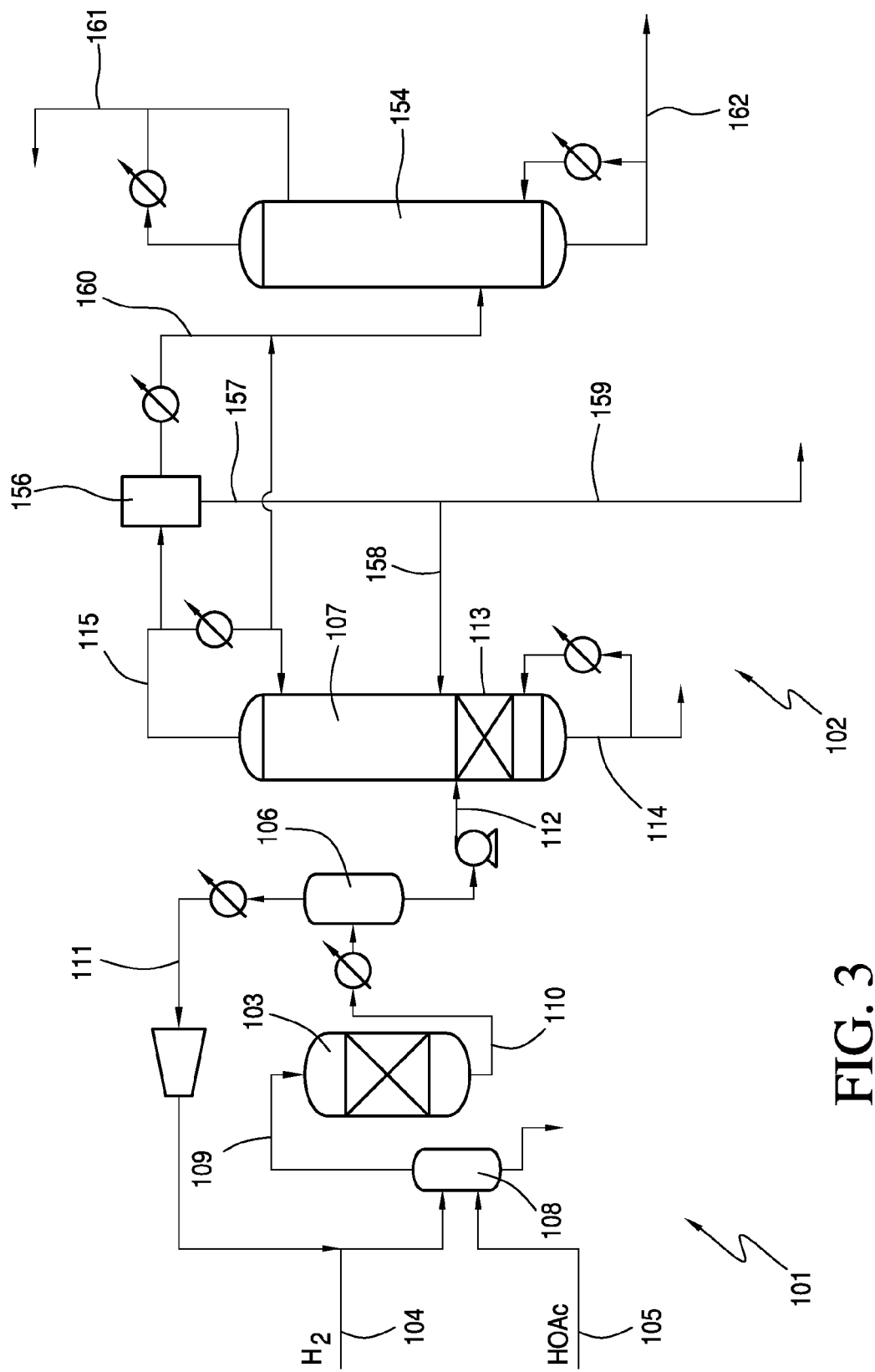
FIG. 3 is a schematic diagram of a hydrogenation/purification system having two columns in accordance with one embodiment of the present invention.

Exemplary ethanol recovery systems in accordance with embodiments of the present invention are shown in FIGS. 1, 2, and 3. Each hydrogenation/purification system 100 provides a suitable hydrogenation reactor and a separation system for separating ethanol from the crude reaction mixture according to an embodiment of the invention. System 100 comprises first reaction zone 101 and separation zone 102. First reaction zone 101 comprises reactor 103, hydrogen feed line 104 and acetic acid feed line 105. Separation zone 102 comprises flasher 106 and separation unit, e.g., first column, 107.

Hydrogen and acetic acid are fed to a vaporizer 108 via lines 104 and 105, respectively, to create a vapor feed stream in line 109 that is directed to first reactor 103. In one embodiment, lines 104 and 105 may be combined and jointly fed to the vaporizer 108. The temperature of the vapor feed stream in line 109 is preferably from 100° C. to 350° C., e.g., from 120° C. to 310° C. or from 150° C. to 300° C. Any feed that is not vaporized is removed from vaporizer 108 and may be recycled or discarded. In addition, although line 109 is shown as being directed to the top of reactor 103, line 109 may be directed to the side, upper portion, or bottom of first reactor 103. Further modifications and additional components to reaction zone 101 and separation zone 102 are described below.

First reactor 103 contains a catalyst that is used in the hydrogenation of the carboxylic acid, preferably acetic acid. In one embodiment, one or more guard beds (not shown) may be used upstream of the reactor to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 103 via line 110.

The crude ethanol product stream in line 110 may be condensed and fed to flasher 106, which, in turn, provides a vapor stream 111 and a liquid stream 112. Of course, other suitable separators may be substituted for flasher 106. As one example, a knock-out pot may be employed. Flasher 106 may operate at a temperature from 20° C. to 250° C., e.g., from 30° C. to 225° C. or from 60° C. to 200° C. The pressure of flasher 106 may be from 50 kPa to 2000 kPa, e.g., from 75 kPa to 1500 kPa or from 100 to 1000 kPa. Optionally, the crude ethanol product in line 110 may pass through one or more membranes to separate hydrogen and/or other non-condensable gases (not shown in FIG. 1).

The vapor stream 111 exiting flasher 106 may comprise hydrogen and hydrocarbons, and may be purged and/or returned to first reaction zone 101. As shown, vapor stream 111 is combined with the hydrogen feed 104 and co-fed to vaporizer 108. In some embodiments, the returned vapor stream 111 may be compressed before being combined with hydrogen feed 104.

The liquid stream 112 from flasher 106 is withdrawn and pumped to the side of separation unit 107. Although a column is shown in FIG. 1, separation unit may be any suitable separation unit, for example, a membrane separation unit. In cases where a column is employed, such a column may be referred to as an "acid separation column." In one embodiment, the contents of liquid stream 112 are substantially similar to the crude ethanol product obtained from the reactor, except that the composition has substantially no hydrogen, carbon dioxide, methane or ethane, which are removed by the flasher 106. Accordingly, liquid stream 112 may also be referred to as a crude ethanol product. Exemplary components of liquid stream 112 are provided in Table 2. It should be understood that liquid stream 112 may contain other components, not listed, such as components derived from the feed.

TABLE 2

FIRST SEPARATION UNIT FEED COMPOSITION

| | Conc. (wt. %) | Conc. (wt. %) | Conc. (wt. %) |
|---|---|---|---|
| Ethanol | 5 to 70 | 15 to 70 | 15 to 50 |
| Acetic Acid | <90 | <50 | 15 to 70 |
| Water | 1 to 30 | 5 to 30 | 10 to 30 |
| Ethyl Acetate | <30 | <20 | 1 to 12 |
| Acetaldehyde | <10 | <3 | 0.1 to 3 |
| Acetal | 0.0005 to 1 | 0.001 to 1 | 0.01 to 1 |
| Acetone | 0 to 90 | 0 to 50 | 15 to 70 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 112 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol product in line 110 or in liquid stream 112 may be further fed to an esterification reactor, hydrolysis reactor (discussed below), or combination thereof. An esterification reactor may be used to consume acetic acid present in the crude ethanol product to further reduce the amount of acetic acid to be removed.

As shown in FIG. 1, liquid stream 112 is introduced in the lower part of first column 107, e.g., lower half or lower third. In one embodiment, no entrainers are added to first column 107. In first column 107, water and unreacted acetic acid, along with any other heavy components, if present, are removed from liquid stream 112 and are withdrawn, preferably continuously, as residue in line 114. First column 107 also forms an overhead distillate, which is withdrawn in line 115, and which may be condensed and refluxed, for example, at a ratio of from 10:1 to 1:10, e.g., from 3:1 to 1:3 or from 1:2 to 2:1. In one embodiment, operating with a reflux ratio of less than 5:1 is preferred.

In accordance with the present invention, a hydrolysis reaction may be used to convert acetals in the crude ethanol product. In some embodiments, the hydrolysis reaction is conducted along with the separation in first separation unit 107. Preferably, diethyl acetal is converted to ethanol and/or acetaldehyde. FIG. 1 shows second reaction zone 113, which hydrolyzes at least a portion of the acetal in the crude ethanol product. In FIG. 1, second reaction zone 113 is shown as a reactor bed, e.g., an ion exchange resin reactor bed. Preferably, the ion exchange resin reactor bed 113 is a gel or macroreticular bed. As shown in FIG. 1, in one embodiment, second reaction zone 113 is disposed within separation unit 107 and the contents of liquid stream 112 may be directed through separation unit 107 and into second reaction zone 113. In some embodiments, ion exchange resin reactor bed 113 is placed above the point at which liquid stream 112 is introduced to the separation unit 107. In other embodiments, ion exchange resin reactor bed 113 is placed at or below the point at which liquid stream 112 is introduced to the separation unit 107. Similar internal ion exchange resin reactor beds may also be used within one or more of the other columns, if other columns are present in the separation zone. Although FIG. 1 shows second reaction zone 113 as a reactor bed, second reaction zone 113 may be any suitable reaction zone capable of performing the hydrolysis reaction.

In cases where separation unit 107 is a column, column 107 may be operated under about 170 kPa, the temperature of the residue exiting in line 114, e.g., by-product stream 114, preferably is from 90° C. to 130° C., e.g., from 95° C. to 120° C. or from 100° C. to 115° C. The base of column 107 may be maintained at a relatively low temperature to withdraw a residue stream comprising both water and acetic acid, thereby providing an energy efficiency advantage that accompanies the conversion advantage achieved by the hydrolysis reaction. The temperature of the distillate exiting in line 115 preferably is from 60° C. to 90° C., e.g., from 65° C. to 85° C. or from 70° C. to 80° C. In some embodiments, the pressure of first column 107 may range from 0.1 kPa to 510 kPa, e.g., from 1 kPa to 475 kPa or from 1 kPa to 375 kPa. Exemplary components of the distillate and residue compositions for first column 107 are provided in Table 3 below. It should also be understood that the distillate and residue may also contain other components, not listed, such as components derived from the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN

|  | Conc. (wt. %) | Conc. (wt. %) | Conc. (wt. %) |
| --- | --- | --- | --- |
| Distillate |  |  |  |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | <90 | 1 to 50 | 2 to 35 |
| Water | 30 to 100 | 45 to 90 | 60 to 90 |
| Ethanol | <1 | <0.9 | <0.5 |

In one embodiment, at high conversions of greater than 90%, acetic acid concentration in the residue may be less than 3 wt. %, e.g. from 0.5 to 3 wt. % or from 1 to 2.9 wt. %. Also, at lower conversions of acetic acid, less than 50%, the water concentration in the residue may be less than 30 wt. %, or less than 20 wt. %, while the acetic acid concentration in the residue may be greater than 40 wt. %, e.g., greater than 60 wt. % or greater than 80 wt. %.

In another embodiment, a reactor bed is not required to conduct the hydrolysis reaction. In some cases, acetals, may decompose, e.g., hydrolyze, in column 107 such that very low amounts, or even no detectable amounts, of acetals remain in the distillate or residue. In these cases, column 107 would comprise second reaction zone 113.

In addition, an equilibrium reaction between acetic acid and ethanol or between ethyl acetate and water may occur in the crude ethanol product after it exits reactor 103. Depending on the concentration of acetic acid in the crude ethanol product, this equilibrium may be driven toward formation of ethyl acetate. This reaction may be regulated using the residence time and/or temperature of crude ethanol product.

Depending on the amount of water and acetic acid contained in the by-product stream, e.g., residue, exiting the first separation unit may be treated via suitable separation processes, some examples of which are discussed herein. It should be understood that any of the following may be used regardless of acetic acid concentration. When the by-product stream, e.g., first column residue, comprises a majority of acetic acid, e.g., greater than 70 wt. %, the residue may be recycled to the reactor without any separation of the water. In one embodiment, the by-product stream may be separated into an acetic acid stream and a water stream when the by-product stream comprises a majority of acetic acid, e.g., greater than 50 wt. %. Acetic acid may also be recovered in some embodiments from a by-product stream having a lower acetic acid concentration. The by-product stream may be separated into the acetic acid and water streams by a distillation column or one or more membranes or via pressure swing absorption. In one embodiment, at least a portion of the water in by-product stream 114 is recovered. Preferably, at least a portion of this recovered water may then be fed to the second reaction zone. In one embodiment the water in the by-product stream is recovered by passing the by-product stream through a pressure swing absorption unit. In another embodiment, the water in the by-product stream is recovered by passing the by-product stream through a membrane separation unit. In either of these cases, a dry by-product stream and a water stream are yielded. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the first reactor. The resulting water stream, as noted above, may be directed to the second reaction zone to hydrolyze the acetals. In another embodiment, the water may be used as an extractive agent in other separation units.

In other embodiments, for example where by-product streams comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility. It also may be possible to separate a by-product stream comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue in line 113 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The refined ethanol stream in line 115 preferably comprises ethanol and optionally ethyl acetate, acetaldehyde, and water. The final ethanol product may be derived from the refined ethanol stream in line 115. In one embodiment, wherein a column is employed as the first separation unit, the weight ratio of water in the residue to the water in the distillate is greater than 1:1, e.g., greater than 2:1 or greater than 4:1. In addition, the weight ratio of acetic acid in the residue to acetic acid in the distillate is optionally greater than 10:1, e.g., greater than 15:1 or greater than 20:1. Preferably, the distillate in line 114 is substantially free of acetic acid and may contain, if any, only trace amounts of acetic acid.

In cases where the first separation unit yields refined ethanol stream 115 in which the hydrolysis step has removed at least a portion of the acetals, one or more additional columns or separation units may be used to recover therefrom a final ethanol product.

For example, FIG. 2 shows a separation scheme that employs multiple columns. The distillate in line 115 preferably comprises ethanol, ethyl acetate, and water, along with other impurities, which may be difficult to separate due to the formation of binary and tertiary azeotropes. To further separate distillate, line 115 is introduced to the second column 123, also referred to as the "light ends column," preferably in the middle part of column 123, e.g., middle half or middle third. Preferably the second column 123 is an extractive distillation column, and an extraction agent is added thereto via lines 124 and/or 125. Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As indicated above, the first distillate in line 115 that is fed to the second column 123 comprises ethyl acetate, ethanol, and water. These compounds tend to form binary and ternary azeotropes, which decrease separation efficiency. As shown, in one embodiment the extraction agent comprises a third residue from line 124. Preferably, the recycled third residue in line 124 is fed to second column 123 at a point higher than the first distillate in line 115. In one embodiment, the recycled third residue in line 124 is fed near the top of second column 123 or fed, for example, above the feed in line 115 and below the reflux line from the condensed overheads. In a tray column, the third residue in line 124 is continuously added near the top of the second column 123 so that an appreciable amount of the third residue is present in the liquid phase on all of the trays below. In another embodiment, the extraction agent is fed from a source outside of the process 100 via line 125 to second column 123. Preferably this extraction agent comprises water.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 123. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 124 and co-fed to the second column 123. The additional extraction agent may also be added separately to the second column 123. In one aspect, the extraction agent comprises an extraction agent, e.g., water, derived from an external source via line 125 and none of the extraction agent is derived from the third residue.

Second column 123 may be a tray or packed column. In one embodiment, second column 123 is a tray column having from 5 to 70 trays, e.g., from 15 to 50 trays or from 20 to 45 trays. Although the temperature and pressure of second column 123 may vary, when at atmospheric pressure the temperature of the second residue exiting in line 126 preferably is from 60° C. to 90° C., e.g., from 70° C. to 90° C. or from 80° C. to 90° C. The temperature of the second distillate exiting in line 127 from second column 123 preferably is from 50° C. to 90° C., e.g., from 60° C. to 80° C. or from 60° C. to 70° C. Column 123 may operate at atmospheric pressure. In other embodiments, the pressure of second column 123 may range from 0.1 KPa to 510 KPa, e.g., from 1 KPa to 475 KPa or from 1 KPa to 375 KPa. Exemplary components for the distillate and residue compositions for second column 123 are provided in Table 4 below. It should be understood that the distillate and residue may also contain other components, not listed, such as components in the feed.

TABLE 4

SECOND COLUMN

| | Conc. (wt. %) | Conc. (wt. %) | Conc. (wt. %) |
|---|---|---|---|
| Distillate | | | |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Acetal | <5 | 0.001 to 2 | 0.01 to 1 |
| Residue | | | |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

In preferred embodiments, the recycling of the third residue promotes the separation of ethyl acetate from the residue of the second column 123. For example, the weight ratio of ethyl acetate in the second residue to second distillate preferably is less than 0.4:1, e.g., less than 0.2:1 or less than 0.1:1. In embodiments that use an extractive distillation column with water as an extraction agent as the second column 123, the weight ratio of ethyl acetate in the second residue to ethyl acetate in the second distillate approaches zero.

The weight ratio of ethanol in the second residue to second distillate preferably is at least 3:1, e.g., at least 6:1, at least 8:1, at least 10:1 or at least 15:1. All or a portion of the third residue is recycled to the second column. In one embodiment, all of the third residue may be recycled until process 100 reaches a steady state and then a portion of the third residue is recycled with the remaining portion being purged from the system 100. The composition of the second residue will tend to have lower amounts of ethanol than when the third residue is not recycled. As the third residue is recycled, the composition of the second residue, as provided in Table 4, comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from second column 123, which comprises ethanol and water, is fed via line 126 to third column 128, also referred to as the "product column." More preferably, the second residue in line 126 is introduced in the lower part of third column 128, e.g., lower half or lower third. Third column 128 recovers ethanol, which preferably is substantially pure with respect to organic impurities and other than the azeotropic water content, as the distillate in line 129. The distillate of third column 128 preferably is refluxed as shown in FIG. 2, for example, at a reflux ratio of from 1:10 to 10:1, e.g., from 1:3 to 3:1 or from 1:2 to 2:1. The third residue in line 124, which comprises primarily water, preferably is returned to the second column 123 as an extraction agent as described above. In one embodiment, a first portion of the third residue in line 124 is recycled to the second column and a second portion is purged and removed from the system via line 130. In one embodiment, once the process reaches steady state, the second portion of water to be purged is substantially similar to the amount water formed in the hydrogenation of acetic acid. In one embodiment, a portion of the third residue may be used to hydrolyze any other stream, such as one or more streams comprising ethyl acetate.

Although FIG. 2 shows third residue being directly recycled to second column 123, third residue may also be returned indirectly, for example, by storing a portion or all of the third residue in a tank (not shown) or treating the third residue to further separate any minor components such as aldehydes, higher molecular weight alcohols, or esters in one or more additional columns (not shown).

Third column 128 is preferably a tray column as described above and operates at atmospheric pressure or optionally at pressures above or below atmospheric pressure. The temperature of the third distillate exiting in line 129 preferably is from 60° C. to 110° C., e.g., from 70° C. to 100° C. or from 75° C. to 95° C. The temperature of the third residue in line 124 preferably is from 70° C. to 115° C., e.g., from 80° C. to 110° C. or from 85° C. to 105° C. Exemplary components of the distillate and residue compositions for third column 128 are provided in Table 5 below. It should be understood that the distillate and residue may also contain other components, not listed, such as components in the feed.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <12 | 0.0001 to 0.1 | 0.005 to 0.05 |
| Ethyl Acetate | <12 | 0.0001 to 0.05 | 0.005 to 0.025 |
| Acetaldehyde | <12 | 0.0001 to 0.1 | 0.005 to 0.05 |
| Diethyl Acetal | <12 | 0.0001 to 0.05 | 0.005 to 0.025 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

In one embodiment, the third residue in line 124 is withdrawn from third column 128 at a temperature higher than the operating temperature of the second column 123. Preferably, the third residue in line 124 is integrated to heat one or more other streams or is reboiled prior to be returned to the second column 123.

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns in the system 100. Preferably at least one side stream is used to remove impurities from the third column 128. The impurities may be purged and/or retained within the system 100.

The third distillate in line 129 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

For purposes of the present invention, the third distillate in line 129 in FIG. 2 is an intermediate stream that contains one or more impurities selected from the group consisting of ethyl acetate, acetic acid, and acetaldehyde, and optionally small amounts of acetal. In terms of ranges the total concentration of impurities may be from 0.01 wt. % to 12 wt. %, e.g., from 0.05 wt. % to 8 wt. % or from 0.05 to 5 wt. %. The scheme of FIG. 2 employs hydrogenation finishing reactor 140. The third distillate in line 129 is condensed and fed to reactor 140 in a liquid phase. Hydrogen may be supplied to reactor 140 on demand from line 113 to react with the impurities in intermediate stream. Also, hydrogen can be supplied from alternate sources, e.g., syngas or purified syngas generated from numerous carbon containing feedstocks. Reactor 140 contains a catalyst as described above to hydrogenate at least 25% of the impurities, e.g., at least 50% or at least 75%. Preferably, the hydrogenation of the impurities yields an alcohol and more preferably ethanol. The reactor mixture exits reactor 140 as purified ethanol product 141. Purified ethanol product 141 preferably does not require further liquid-liquid separation to remove impurities and thus is not returned to separation zone 102. The concentration of the one or more impurities in purified ethanol product 141 is less than the concentration of the one or more impurities in third distillate in line 129, i.e., the intermediate stream.

Returning to second column 123, the second distillate preferably is refluxed as shown in FIG. 2, optionally at a reflux ratio of 1:10 to 10:1, e.g., from 1:5 to 5:1 or from 1:3 to 3:1. The second distillate in line 127 may be purged or recycled to the reaction zone. In one embodiment, the second distillate in line 127 is further processed in a fourth column 131, also referred to as the "acetaldehyde removal column." In fourth column 131 the second distillate is separated into a fourth distillate, which comprises acetaldehyde, in line 132 and a fourth residue, which comprises ethyl acetate, in line 133. The fourth distillate preferably is refluxed at a reflux ratio of from 1:20 to 20:1, e.g., from 1:15 to 15:1 or from 1:10 to 10:1, and a portion of the fourth distillate is returned to the reaction zone 101. For example, the fourth distillate may be combined with the acetic acid feed, added to the vaporizer 106, or added directly to the reactor 103. The fourth distillate preferably is co-fed with the acetic acid in feed line 105 to vaporizer 106. Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of fourth column 131 may be purged via line 133. The fourth residue primarily comprises ethyl acetate and ethanol, which may be suitable for use as a solvent mixture or in the production of esters. In one preferred embodiment, the acetaldehyde is removed from the second distillate in fourth column 131 such that no detectable amount of acetaldehyde is present in the residue of column 131.

Fourth column 131 is preferably a tray column as described above and preferably operates above atmospheric pressure. In one embodiment, the pressure is from 120 KPa to 5,000 KPa, e.g., from 200 KPa to 4,500 KPa, or from 400 KPa to 3,000 KPa. In a preferred embodiment the fourth column 131 may operate at a pressure that is higher than the pressure of the other columns.

The temperature of the fourth distillate exiting in line 132 preferably is from 60° C. to 110° C., e.g., from 70° C. to 100° C. or from 75° C. to 95° C. The temperature of the residue in line 133 preferably is from 70° C. to 115° C., e.g., from 80° C. to 110° C. or from 85° C. to 110° C. Exemplary components of the distillate and residue compositions for fourth column 131 are provided in Table 7 below. It should be understood that the distillate and residue may also contain other components, not listed, such as components in the feed.

TABLE 6

FOURTH COLUMN

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

In one embodiment, a portion of the third residue in line 124 is recycled to second column 123. In one embodiment, recycling the third residue further reduces the aldehyde components in the second residue and concentrates these aldehyde components in second distillate in line 127 and thereby sent to the fourth column 131, wherein the aldehydes may be more easily separated. The third distillate, e.g. intermediate stream, in line 129 may have lower concentrations of aldehydes and esters due to the recycling of third residue in line 124.

FIG. 3 illustrates another exemplary separation system. The primary reaction zone 101 of FIG. 3 is similar to that of FIGS. 1 and 2 and produces liquid stream 112, e.g., crude ethanol product, for further separation. In one preferred embodiment, the primary reaction zone 101 of FIG. 3 operates at above 80% acetic acid conversion, e.g., above 90% conversion or above 99% conversion. Thus, the acetic acid concentration in the liquid stream 112 may be low.

Liquid stream 112 is introduced in the middle or lower portion of first column 107, which, in these embodiments, may be referred to as acid-water column. In one embodiment, no entrainers are added to first column 107. In FIG. 3, first column 107, water and unreacted acetic acid, along with any other heavy components, if present, are removed from liquid stream 112 and are withdrawn, preferably continuously, as a first residue in line 114, e.g., by-product stream 114. Preferably, a substantial portion of the water in the crude ethanol product that is fed to first column 107 may be removed in the first residue, for example, up to about 75% or to about 90% of the water from the crude ethanol product. First column 107 also forms a first distillate, which is withdrawn in line 115, e.g., refined ethanol stream 115.

When column 107 is operated under about 170 kPa, the temperature of the residue exiting in line 114 preferably is from 90° C. to 130° C., e.g., from 95° C. to 120° C. or from 100° C. to 115° C. The temperature of the distillate exiting in line 115 preferably is from 60° C. to 90° C., e.g., from 65° C. to 85° C. or from 70° C. to 80° C. In some embodiments, the pressure of first column 107 may range from 0.1 kPa to 510 kPa, e.g., from 1 kPa to 475 kPa or from 1 kPa to 375 kPa.

The first distillate in line 115 comprises water, in addition to ethanol and other organics. In terms of ranges, the concentration of water in the first distillate in line 115 preferably is from 4 wt. % to 38 wt. %, e.g., from 7 wt. % to 32 wt. %, or from 7 to 25 wt. %. A portion of first distillate in line 115 may be condensed and refluxed, for example, at a ratio of from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 107. The condensed portion of the first distillate may also be fed to a second column 154.

The remaining portion of the first distillate in line 115 is fed to a water separation unit 156. Water separation unit 156 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 156 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds. Water separator 156 may remove at least 95% of the water from the portion of first distillate in line 155, and more preferably from 99% to 99.99% of the water from the first distillate, in a water stream 157. All or a portion of water stream 157 may be returned via line 158 to column 107 and/or or second reaction zone 113, where the water preferably is ultimately recovered from column 107 in the first residue in line 114. Additionally or alternatively, all or a portion of water stream 157 may be purged via line 159. The remaining portion of first distillate exits the water separator 156 as ethanol mixture stream 160. Ethanol mixture stream 160 may have a low concentration of water of less than 10 wt. %, e.g., less than 6 wt. % or less than 2 wt. %. Exemplary components of ethanol mixture stream 160 and first residue in line 115 are provided in Table 7 below. It should also be understood that these streams may also contain other components, not listed, such as components derived from the feed.

TABLE 7

FIRST COLUMN WITH PSA

|  | Conc. (wt. %) | Conc. (wt. %) | Conc. (wt. %) |
|---|---|---|---|
| Ethanol Mixture Stream |  |  |  |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |

TABLE 7-continued

FIRST COLUMN WITH PSA

| | Conc. (wt. %) | Conc. (wt. %) | Conc. (wt. %) |
|---|---|---|---|
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | <90 | 1 to 50 | 2 to 35 |
| Water | 30 to 100 | 45 to 95 | 60 to 90 |
| Ethanol | <1 | <0.9 | <0.3 |

Preferably, ethanol mixture stream 160 is not returned or refluxed to first column 107. The condensed portion of the first distillate in line 153 may be combined with ethanol mixture stream 160 to control the water concentration fed to the second column 154. For example, in some embodiments the first distillate may be split into equal portions, while in other embodiments, all of the first distillate may be condensed or all of the first distillate may be processed in the water separation unit. In FIG. 3, the condensed portion in line 153 and ethanol mixture stream 160 are co-fed to second column 154. In other embodiments, the condensed portion in line 153 and ethanol mixture stream 160 may be separately fed to second column 154. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 154 in FIG. 3, also referred to as the "light ends column," removes ethyl acetate and acetaldehyde from the first distillate in line 153 and/or ethanol mixture stream 160. Ethyl acetate and acetaldehyde are removed as a second distillate in line 161 and ethanol is removed as the second residue in line 162. Second column 154 may be a tray column or packed column. In one embodiment, second column 154 is a tray column having from 5 to 70 trays, e.g., from 15 to 50 trays or from 20 to 45 trays.

Second column 154 operates at a pressure ranging from 0.1 kPa to 510 kPa, e.g., from 10 kPa to 450 kPa or from 50 kPa to 350 kPa. Although the temperature of second column 154 may vary, when at about 20 kPa to 70 kPa, the temperature of the second residue exiting in line 162 preferably is from 30° C. to 75° C., e.g., from 35° C. to 70° C. or from 40° C. to 65° C. The temperature of the second distillate exiting in line 161 preferably is from 20° C. to 55° C., e.g., from 25° C. to 50° C. or from 30° C. to 45° C.

The total concentration of water fed to second column 154 preferably is less than 10 wt. %, as discussed above. When first distillate in line 153 and/or ethanol mixture stream comprises minor amounts of water, e.g., less than 1 wt. % or less than 0.5 wt. %, additional water may be fed to the second column 154 as an extractive agent in the upper portion of the column. A sufficient amount of water is preferably added via the extractive agent such that the total concentration of water fed to second column 154 is from 1 to 10 wt. % water, e.g., from 2 to 6 wt. %, based on the total weight of all components fed to second column 154. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate and second residue compositions for the second column 154 are provided in Table 8, below. It should be understood that the distillate and residue may also contain other components, not listed in Table 9.

TABLE 8

SECOND COLUMN

| | Conc. (wt. %) | Conc. (wt. %) | Conc. (wt. %) |
|---|---|---|---|
| Second Distillate | | | |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Second Residue | | | |
| Ethanol | 80 to 99.5 | 85 to 97 | 60 to 95 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |

The second residue in FIG. 3 is the intermediate stream that comprises one or more impurities selected from the group consisting of ethyl acetate, acetic acid, acetaldehyde, and diethyl acetal. The second residue in line 162 may comprise at least 100 wppm of these impurities, e.g., at least 250 wppm or at least 500 wppm. In some embodiments, the second residue may contain substantially no ethyl acetate or acetaldehyde.

In one embodiment, second residue in line 162 may be further processed, e.g., fed to a hydrogenation finishing reactor, along with hydrogen from the primary reaction zone. Preferably, the second residue is fed in the liquid phase. The hydrogenation finishing reactor produces a purified ethanol product having a lower concentration of impurities than the second residue. Preferably, the purified ethanol product does not require further liquid-liquid separation to remove impurities and thus is not returned to separation zone.

Ethanol Compositions

Exemplary finished ethanol compositional ranges are provided below in Table 9.

TABLE 9

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.1 | <0.05 | <0.01 |
| Acetone | <0.05 | <0.01 | <0.005 |
| Isopropanol | <0.5 | <0.1 | <0.05 |
| n-propanol | <0.5 | <0.1 | <0.05 |

As shown in Table 9, because of the hydrolysis step, the finished ethanol compositions of the present invention contain little of no acetals and/or acetates. In addition, the finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 9, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, an example is provided below. It should be understood that these examples are for illustrative purposes only and is not to be construed as limiting the invention in any manner.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for purifying a crude ethanol product, comprising the steps of:
   (a) hydrogenating acetic acid in a first reaction zone in the presence of a first catalyst to form the crude ethanol product comprising ethanol, acetaldehyde, acetic acid, water, and acetal;
   (b) separating at least a portion of the crude ethanol product into a refined ethanol stream comprising ethanol and acetaldehyde; and a by-product stream comprising acetic acid and a substantial portion of the water from the crude ethanol product; and
   (c) hydrolyzing in a second reaction zone at least a portion of the acetal in at least one of the crude ethanol product or the refined ethanol stream in the presence of an acidic catalyst at a temperature of between 90 and 130° C., wherein the second reaction zone comprises a catalyst bed.

2. The process of claim 1, further comprising the steps of: feeding the at least a portion of the by-product stream back to the second reaction zone.

3. The process of claim 1, further comprising the steps of: recovering at least a portion of the water from the by-product stream; and feeding the recovered water back to the second reaction zone.

4. The process of claim 3, wherein the recovering comprises passing the by-product stream through a pressure swing adsorption system to yield a dry by-product stream and a water stream.

5. The process of claim 3, wherein the recovering comprises passing the by-product stream through a membrane to yield a dry by-product stream and a water stream.

6. The process of claim 1, wherein the refined ethanol stream further comprises water and further comprising the steps of:
   recovering at least a portion of the water from the refined ethanol stream; and
   feeding the recovered water back to the second reaction zone.

7. The process of claim 1, wherein the acetal comprises diethyl acetal.

8. The process of claim 1, wherein at least a portion of the acetal is hydrolyzed to form additional ethanol.

9. The process of claim 1, wherein at least a portion of the acetal is hydrolyzed to form acetaldehyde and additional ethanol.

10. The process of claim 1, wherein at least one of the crude ethanol product, refined ethanol product and by-product stream further comprise ethyl acetate, and wherein the ethyl acetate is hydrolyzed to form ethanol and acetic acid.

11. The process of claim 1, wherein the step (c) is conducted in the liquid phase.

12. The process of claim 1, wherein the first catalyst is selected from the group consisting of a combination metals selected from the group consisting of platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron.

13. The process of claim 1, wherein step (b) is conducted in a first column.

14. The process of claim 13, wherein the refined ethanol stream comprises a first distillate and the by-product stream comprises a first residue.

15. The process of claim 13, wherein the first column comprises the second reaction zone.

16. The process of claim 13, wherein the first column is a reactive distillation column.

17. A process for purifying a crude ethanol product, comprising the steps of:
   (a) hydrogenating acetic acid in a first reaction zone in the presence of a first catalyst to form the crude ethanol product comprising ethanol, acetaldehyde, acetic acid, water, and acetal;
   (b) separating at least a portion of the crude ethanol product into a refined ethanol stream comprising ethanol and acetaldehyde; and a by-product stream comprising acetic acid and a substantial portion of the water from the crude ethanol product;
   (c) separating at least a portion of the refined ethanol stream in a second column into a second distillate comprising acetaldehyde and a second residue comprising ethanol; and
   (d) hydrolyzing in a second reaction zone at least a portion of the acetal in the presence of an acidic catalyst at a temperature of between 90 and 130° C.; wherein the second column comprises the second reaction zone.

18. The process of claim 17, wherein the second column is operated at a pressure ranging from 0.1 kPa to 510 kPa.

19. The process of claim 1, wherein step (b) is conducted in a membrane separation unit.

20. The process of claim 1, wherein the crude ethanol product comprises less than 10 wt % ethyl acetate.

21. The process of claim 1, wherein the crude ethanol product comprises less than 1 wt % acetal.

22. The process of claim 1, wherein the crude ethanol product comprises from 1 wt % to 30 wt % water.

23. The process of claim 1, wherein the by-product stream comprises greater than 30 wt. % water.

24. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

25. A process for purifying a crude ethanol product, comprising the steps of:
   (a) hydrogenating acetic acid in a first reaction zone in the presence of a first catalyst to form the crude ethanol product, wherein the crude ethanol product comprises ethanol, acetaldehyde, acetic acid, acetal and ethyl acetate;
   (b) hydrolyzing the acetal and ethyl acetate from the crude ethanol product in a second reaction zone in the presence of an acidic catalyst at a temperature of between 90 and 130° C.; and
   (c) separating at least a portion of the crude ethanol product in a first column into a first distillate comprising ethanol and acetaldehyde, and a first residue comprising water.

26. The process of claim 25, wherein the first residue further comprises water from the crude ethanol product.

27. The process of claim 26, further comprising the steps of:
   recovering water from the first residue and
   feeding the recovered water back to the first column.

* * * * *